(12) United States Patent
Webb et al.

(10) Patent No.: US 6,255,310 B1
(45) Date of Patent: Jul. 3, 2001

(54) THIOPHENOPYRIMIDINES

(75) Inventors: Thomas R. Webb, Olivenhain; Chen Chen, San Diego; James R. McCarthy, Solana Beach; Terence J. Moran, San Diego, all of CA (US)

(73) Assignee: Neurocrine Biosciences Inc., San Diego, CA (US)

( * ) Notice: Subject to any disclaimer, the term of this patent is extended or adjusted under 35 U.S.C. 154(b) by 0 days.

(21) Appl. No.: 09/117,715

(22) PCT Filed: Jan. 30, 1997

(86) PCT No.: PCT/EP97/00457

§ 371 Date: Dec. 28, 1998

§ 102(e) Date: Dec. 28, 1998

(87) PCT Pub. No.: WO97/29110

PCT Pub. Date: Aug. 14, 1997

Related U.S. Application Data

(60) Provisional application No. 60/027,689, filed on Oct. 8, 1996, and provisional application No. 60/011,274, filed on Feb. 7, 1996.

(51) Int. Cl.⁷ .......................... A61K 31/519; A61P 5/04; A61P 25/18; C07D 495/04
(52) U.S. Cl. ............................. 514/258; 544/278
(58) Field of Search .............................. 544/278; 514/258

(56) References Cited

U.S. PATENT DOCUMENTS 5,063,245    11/1991    Abreu et al. .................. 548/365

FOREIGN PATENT DOCUMENTS

| 2 121 950 | 11/1972 | (DE) . |
| 0 071 227 | 2/1983 | (EP) . |
| 0 452 002 | * 10/1991 | (EP) . |
| WO 94/13676 | 6/1994 | (WO) . |
| WO 94/13677 | 6/1994 | (WO) . |
| WO 95/33750 | 12/1995 | (WO) . |
| WO 96/35689 | 11/1996 | (WO) . |

OTHER PUBLICATIONS

Shishoo, C.J., et al., "Synthesis of some 2–substituted–6–phenyl–and 7–phenyl–thieno[3,2–d]pyrimidin–4(3H)–ones", Indian Journal of Chemistry, vol. 33B, May 1994, pp. 436–440.

Shishoo et al. Indian J. Chem, Sect. B. Org. Chem 33B(5), 436–40, 1994.*

* cited by examiner

Primary Examiner—Richard L. Raymond
Assistant Examiner—Venkataraman Balasubramanian
(74) Attorney, Agent, or Firm—Scully, Scott, Murphy & Presser

(57) ABSTRACT

This invention concerns compounds of formula

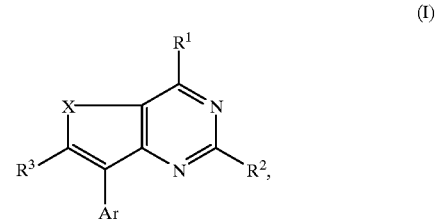

(I)

including the stereoisomers and the pharmaceutically acceptable acid addition salt forms thereof, wherein X is S, SO or $SO_2$; $R^1$ is $NR^4R^5$ or $OR^5$; $R^2$ is $C_{1-6}$alkyl, $C_{1-6}$alkyloxy or $C_{1-6}$alkylthio; $R^3$ is hydrogen, $C_{1-6}$alkyl, $C_{1-6}$alkylsulfonyl, $C_{1-6}$alkylsulfoxy or $C_{1-6}$alkylthio; $R^4$ is hydrogen, $C_{1-6}$alkyl, mono- or di($C_{3-6}$cycloalkyl)methyl, $C_{3-6}$cycloalkyl, $C_{3-6}$alkenyl, hydroxy$C_{1-6}$alkyl, $C_{1-6}$alkylcarbonyloxy$C_{1-6}$alkyl or $C_{1-6}$alkyloxy$C_{1-6}$alkyl; $R^5$ is $C_{1-8}$alkyl, mono- or di($C_{3-6}$cycloalkyl)methyl, $Ar^1CH_2$, $C_{1-6}$alkyloxy-$C_{1-6}$alkyl, hydroxy$C_{1-6}$alkyl, $C_{3-6}$alkenyl, thienylmethyl, furanylmethyl, $C_{1-6}$alkylthio $C_{1-6}$alkyl, morpholinyl, mono- or di($C_{1-6}$alkyl)amino$C_{1-6}$alkyl, di($C_{1-6}$alkyl)amino, $C_{1-6}$alkylcarbonyl$C_{1-6}$alkyl, $C_{1-6}$alkyl substituted with imidazolyl; or a radical of formula —Alk—O—CO—$Ar^1$; or $R^4$ and $R^5$ taken together with the nitrogen atom to which they are attached may form an optionally substituted pyrrolidinyl, piperidinyl, homopiperidinyl or morpholinyl group; Ar is phenyl, substituted phenyl, pyridinyl or substituted pyridinyl; having CRF receptor antagonistic properties; pharmaceutical compositions containing such compounds as active ingredients; methods of treating disorders related to hypersecretion of CRF such as depression, anxiety, substance abuse, by administering an effective amount of a compound of formula (I).

20 Claims, No Drawings

THIOPHENOPYRIMIDINES

This application is a 371 of PCT/EP97/00457 filed Jan. 30, 1997 which claims benefit of U.S. Provisional Application Nos. 60/011,274, filed Feb. 7, 1996 and 60/027,689 filed Oct. 8, 1996.

BACKGROUND OF THE INVENTION

This invention relates to thiophenopyrimidines which possess CRF receptor antagonistic properties, to pharmaceutical compositions containing these compounds as active ingredient, and the use thereof in the treatment of endocrine, psychiatric and neurologic conditions or illnesses, including stress-related disorders in general.

The first corticotropin-releasing factor (CRF) was isolated from ovine hypothalmi and identified as a 41-amino acid peptide (Vale et al., Science 213:1394–1397, 1981). Subsequently, sequences of human and rat CRF were isolated and determined to be identical, but different from ovine CRF in 7 of the 41 amino acid residues (Rivier et al., Proc. Natl. Acad. Sci. USA 80:4851, 1983; Shibahara et al., EMBO J. 2:775, 1983). CRF has been found to produce profound alterations in endocrine, nervous and immune system functions. CRF is believed to be the major physiological regulator of the basal and stress-release of adrenocorticotropic hormone ("ACTH"), β-endorphin, and other pro-opiomelanocortin ("POMC")-derived peptides from the anterior pituitary (Vale et al., Science 213:1394–1397, 1981). Briefly, CRF is believed to initiate its biological effects by binding to a plasma membrane receptor which has been found to be distributed throughout the brain (DeSouza et al., Science 221:1449–1451, 1984), pituitary (DeSouza et al., Methods Enzymol. 124:560, 1986; Wynn et al., Biochem. Biophys. Res. Comm. 110:602–608, 1983), adrenals (Udelsman et al., Nature 319:147–150, 1986) and spleen (Webster, E. L., and E. B. DeSouza, Endocrinology 122:609–617, 1988). The CRF receptor is coupled to a GTP-binding protein (Perrin et al., Endocrinology 118:1171–1179, 1986) which mediates CRF-stimulated increase in intracellular production of cAMP (Bilezikjian, L. M., and W. W. Vale, Endocrinology 113:657–662, 1983).

In addition to its role in stimulating the production of ACTH and POMC, CRF is also believed to coordinate many of the endocrine autonomic, and behavioral responses to stress, and may be involved in the pathophysiology of affective disorders. Moreover, CRF is believed to be a key intermediary in communication between the immune, central nervous, endocrine and cardiovascular systems (Crofford et al., J. Clin. Invest. 90:2555–2564, 1992; Sapolsky et al., Science 238:522–524, 1987; Tilders et al., Regul. Peptides 5:77–84, 1982). Overall, CRF appears to be one of the pivotal central nervous system neurotransmitters and plays a crucial role in integrating the body's overall response to stress.

Administration of CRF directly to the brain elicits behavioral, physiological, and endocrine responses identical to those observed for an animal exposed to a stressful environment. For example, intracerebroventricular injection of CRF results in behavioral activation (Sutton et al., Nature 297:331, 1982), persistent activation of the electroencephalogram (Ehlers et al., Brain Res. 2/8332, 1983), stimulation of the sympathoadrenomedullary pathway (Brown et al., Endocrinology 110:928, 1982), an increase of heart rate and blood pressure (Fisher et al., Endocrinology 110:2222, 1982), an increase in oxygen consumption (Brown et al., Life Sciences 30:207, 1982), alteration of gastrointestinal activity (Williams et al., Am. J. Physiol. 253:G582, 1987), suppression of food consumption (Levine et al., Neuropharmacology 22:337, 1983), modification of sexual behavior (Sirinathsinghji et al., Nature 305:232, 1983), and immune function compromise (Irwin et al., Am. J. Physiol. 255:R744, 1988). Furthermore, clinical data suggest that CRF may be hypersecreted in the brain in depression, anxiety-related disorders, and anorexia nervosa. (DeSouza, Ann. Reports in Med. Chem. 25:215–223, 1990).

Accordingly, clinical data suggest that CRF receptor antagonists may represent novel antidepressant and/or anxiolytic drugs that may be useful in the treatment of the neuropsychiatric disorders manifesting hypersecretion of CRF. CRF receptor antagonists have been reported in for example, U.S. Pat. No. 5,063,245 disclosing substituted 4-thio-5-oxo-3-pyrazoline derivatives and Australian Patent No. AU-A-41399/93, disclosing substituted 2-aminothiazole derivatives. Also, WO-94/13676, WO-94/13677 and WO-95/33750 disclose pyrrolopyrimidines, pyrazolo[3,4-d] pyrimidines and substituted purines as CRF receptor antagonists. EP-0,452,002 discloses thienopyrimidines as pesticides.

Due to the physiological significance of CRF, the development of further biologically active small molecules having significant CRF receptor binding activity and which are capable of antagonizing the CRF receptor remains a desirable goal. Such CRF receptor antagonists would be useful in the treatment of endocrine, psychiatric and neurologic conditions or illnesses, including stress-related disorders in general.

DESCRIPTION OF THE INVENTION

This invention concerns compounds of formula

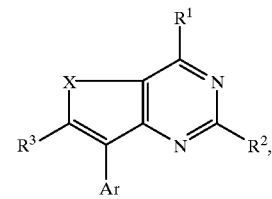

(I)

including the stereoisomers and the pharmaceutically acceptable acid addition salt forms thereof, wherein X is S, SO or $SO_2$;

$R^1$ is $NR^4R^5$ or $OR^5$;

$R^2$ is $C_{1-6}$alkyl, $C_{1-6}$alkyloxy or $C_{1-6}$alkylthio;

$R^3$ is hydrogen, $C_{1-6}$alkyl, $C_{1-6}$alkylsulfonyl, $C_{1-6}$alkylsulfoxy or $C_{1-6}$alkylthio;

$R^4$ is hydrogen, $C_{1-6}$alkyl, mono- or di($C_{3-6}$cycloalkyl)methyl, $C_{3-6}$cycloalkyl, $C_{3-6}$alkenyl, hydroxy$C_{1-6}$alkyl, $C_{1-6}$alkylcarbonyloxy$C_{1-6}$alkyl or $C_{1-6}$alkyloxy$C_{1-6}$alkyl;

$R^5$ is $C_{1-8}$alkyl, mono- or di($C_{3-6}$cycloalkyl)methyl, $Ar^1CH_2$, $C_{1-6}$alkyloxy$C_{1-6}$alkyl, hydroxy$C_{1-6}$alkyl, $C_{3-6}$alkenyl, thienylmethyl, furanylmethyl, $C_{1-6}$alkylthio$C_{1-6}$alkyl, morpholinyl, mono- or di($C_{1-6}$alkyl)amino$C_{1-6}$alkyl, di($C_{1-6}$alkyl)amino, $C_{1-6}$alkylcarbonyl$C_{1-6}$alkyl, $C_{1-6}$alkyl substituted with imidazolyl; or a radical of formula —Alk—O—CO—$Ar^1$;

or $R^4$ and $R^5$ taken together with the nitrogen atom to which they are attached may form a pyrrolidinyl, piperidinyl, homopiperidinyl or morpholinyl group, optionally substituted with $C_{1-6}$alkyl or $C_{1-6}$alkyloxy$C_{1-6}$alkyl;

Ar is phenyl; phenyl substituted with 1, 2 or 3 substituents independently selected from halo, $C_{1-6}$alkyl, trifluoromethyl, hydroxy, cyano, $C_{1-6}$alkyloxy, benzyloxy, $C_{1-6}$alkylthio, nitro, amino and mono- or di($C_{1-6}$alkyl)amino; pyridinyl; pyridinyl substituted with 1, 2 or 3 substituents independently selected from halo, $C_{1-6}$alkyl, trifluoromethyl, hydroxy, cyano, $C_{1-6}$alkyloxy, benzyloxy, $C_{1-6}$alkylthio, nitro, amino, mono- or di($C_{1-6}$alkyl)amino and piperidinyl; and wherein said substituted phenyl may optionally be further substituted with one or more halogens;

$Ar^1$ is phenyl; phenyl substituted with 1, 2 or 3 substituents each independently selected from halo, $C_{1-6}$alkyl, $C_{1-6}$alkyloxy, di($C_{1-6}$alkyl)amino$C_{1-6}$alkyl, trifluoromethyl and $C_{1-6}$alkyl substituted with morpholinyl; or pyridinyl; and Alk is $C_{1-6}$alkanediyl.

As used in the foregoing definitions and hereinafter, halo is generic to fluoro, chloro, bromo and iodo; $C_{1-6}$alkanediyl defines bivalent straight and branched chained saturated hydrocarbon radicals having from 1 to 6 carbon atoms, such as, for example, methylene, 1,2-ethanediyl, 1,3-propanediyl, 1,4-butanediyl, 1,5-pentanediyl, 1,6-hexanediyl and the branched isomers thereof; $C_{1-2}$alkyl defines straight saturated hydrocarbon radicals having from 1 to 2 carbon atoms such as methyl and ethyl; $C_{2-4}$alkyl defines straight and branched chain saturated hydrocarbon radicals having from 2 to 4 carbon atoms such as ethyl, propyl, butyl, 1-methylethyl and the like; $C_{3-4}$alkyl defines straight and branched chain saturated hydrocarbon radicals having from 3 to 4 carbon atoms such as propyl, butyl, 1-methylethyl and the like; $C_{1-6}$alkyl includes $C_{1-2}$alkyl and $C_{3-4}$alkyl radicals as defined hereinbefore and the higher homologs thereof having from 5 to 6 carbon atoms such as, pentyl, the pentyl isomers, hexyl and the hexyl isomers; $C_{1-8}$alkyl includes $C_{1-6}$alkyl and the higher homologues thereof having from 7 to 8 carbon atoms such as, for example, heptyl, octyl and the like; $C_{3-6}$alkenyl defines straight and branched chain hydrocarbon radicals containing one double bond and having from 3 to 6 carbon atoms such as, for example, 2-propenyl, 3-butenyl, 2-pentenyl, 3-pentenyl, 3-methyl-2-butenyl, and the like; and where said $C_{3-6}$alkenyl is linked to a nitrogen or oxygen, the carbon atom making the link preferably is saturated. $C_{3-6}$cycloalkyl comprises cyclopropyl, cyclobutyl, cyclopentyl and cyclohexyl. Hydroxy$C_{1-6}$alkyl refers to $C_{1-6}$alkyl substituted with a hydroxylgroup. Homopiperidinyl refers to a 7 membered saturated ring containing one nitrogen atom.

Depending on the nature of some of the substituents, the compounds of formula (I) may contain one or more asymmetric centers which may be designated with the generally used R and S nomenclature.

The compounds of the present invention contain basic nitrogen atoms and, as such, can be present as the free base or in the form of acid addition salts, both being part of this invention. Acid addition salts may be prepared by methods well known in the art, and may be formed from organic and inorganic acids. Suitable organic acids include maleic, fumaric, benzoic, ascorbic, succinic, methanesulfonic, acetic, oxalic, propionic, tartaric, salicylic, citric, gluconic, lactic, mandelic, cinnamic, aspartic, stearic, palmitic, glycolic, glutamic, and benzenesulfonic acids. Suitable inorganic acids include hydrochloric, hydrobromic, sulfuric, phosphoric, and nitric acids.

Particular groups of compounds within the invention are those compounds of formula (I) wherein one or more of the following restrictions apply:

a) $R^1$ is $NR^4R^5$ wherein $R^4$ is $C_{1-6}$alkyl or $C_{1-6}$alkyloxy$C_{1-6}$alkyl, and $R^5$ is $C_{1-6}$alkyl, $C_{3-6}$alkenyl, $C_{3-6}$cycloalkylmethyl or hydroxy$C_{1-6}$alkyl; in particular $R^4$ is $C_{2-4}$alkyl or methoxy$C_{1-2}$alkyl, and $R^5$ is $C_{2-4}$alkyl, cyclopropylmethyl or hydroxy$C_{2-4}$alkyl;

b) or, $R^1$ is $OR^5$ wherein $R^5$ is $C_{1-6}$alkyl; in particular $C_{2-4}$alkyl;

c) $R^2$ is $C_{1-6}$alkyl, in particular $C_{1-2}$alkyl;

d) $R^3$ is hydrogen or $C_{1-6}$alkyl, in particular hydrogen or $C_{1-2}$alkyl;

e) Ar is a phenyl substituted with 1, 2 or 3 substituents each independently selected from $C_{1-6}$alkyl, $C_{1-6}$alkyloxy or halo and one of the further hydrogens on said substituted phenyl may be a halo; in particular Ar is phenyl substituted on the 4-, 2,4- or 2,4,6-positions each independently with halo, $C_{1-2}$alkyl or $C_{1-2}$alkyloxy; or Ar is a pyridinyl substituted with 1, 2 or 3 substituents each independently selected from di($C_{1-6}$alkyl)amino or $C_{1-6}$alkyl; in particular Ar is pyridinyl substituted on the 2,4-, 2,6- or 2,4,6-positions each independently with di($C_{1-2}$alkyl)amino or $C_{1-2}$alkyl.

Another particular group of compounds are those compounds of formula (I) wherein $R^1$ is $NR^4R^5$ and $R^4$ and $R^5$ are taken together with the nitrogen atom to which they are attached to form a pyrrolidinyl, piperidinyl, homopiperidinyl or morpholinyl group; optionally substituted with $C_{1-6}$alkyl or $C_{1-6}$alkyloxy$C_{1-6}$alkyl.

Preferred compounds are those compounds of formula (I) wherein $R^1$ is $NR^4R^5$ wherein $R^4$ is $C_{3-4}$alkyl or $C_{1-2}$alkyloxy$C_{3-4}$alkyl, preferably propyl; and $R^5$ is $C_{3-4}$alkyl or cyclopropylmethyl, preferably propyl; or $R^1$ is $OR^5$ wherein $R^5$ is $C_{3-4}$alkyl; $R^2$ is methyl; $R^3$ is hydrogen or methyl; and Ar is substituted in the 2-, 4- and 6-positions with halo or $C_{1-4}$alkyl and optionally further substituted with a 3-halo; more preferably Ar is 2,4,6-trimethyl-phenyl, 3-bromo-2,4,6-trimethylphenyl, 6-(dimethylamino)-4-methyl-pyridinyl or 2,4-dimethylpyridinyl.

More preferably Ar is 3-pyridinyl substituted in the 4- and/or 6-position with methyl or dimethylamino.

Most preferred are those compounds selected from 2-methyl-6-(N-propyl-N-cyclopropylamino)-8-(2,4,6-trimethylphenyl)thiopheno[3,2-d]pyrimidine; or 2-methyl-6-(N,N-dipropylamino)-8-(2,4,6-trimethylphenyl)-thiopheno[3,2-d]pyrimidine; the stereoisomeric forms and the pharmaceutically acceptable acid addition salts thereof.

The compounds of the present invention can generally be prepared by alkylating a thiazolopyrimidine of formula (II) with an intermediate of formula (III).

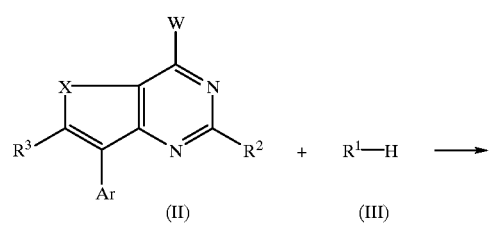

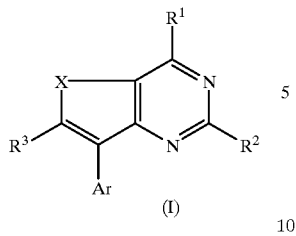

(I)

In intermediate (II), W is an appropriate leaving group such as halo, e.g. chloro, bromo, or a sulfonyloxy group, e.g. a mesyloxy or a tosyloxy group. The above reaction is typically conducted in a suitable solvent, e.g. an aprotic solvent such as DMF or acetonitrile, an ether, e.g. tetrahydrofuran, preferably at an elevated temperature and, when intermediates of formula (III) are volatile amines, in a sealed reaction vial.

Also, compounds of formula (I) wherein $R^1$ is $OR^5$, said compounds being represented by formula (I-a), may be prepared by O-alkylating an intermediate of formula (IX) with an intermediate of formula (X), wherein W is as defined above. Said reaction can be performed in a reaction-inert solvent such as, for example, N,N-dimethylformamide, and in the presence of a suitable base such as, for example, sodium hydride, preferably at a temperature ranging between room temperature and reflux temperature.

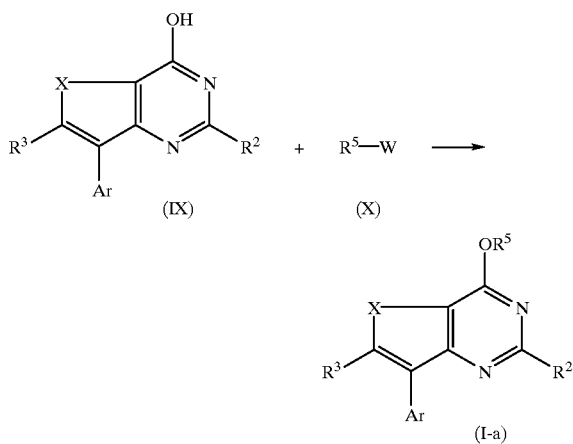

(IX)    (X)

(I-a)

The compounds of formula (I) wherein $R^1$ is $NR^4R^5$, represented by formula (I-c), can be prepared from either compounds of formula (XI) or (XII) by suitable N-alkylation reactions as depicted herebelow, wherein W is as previously defined. These N-alkylations are conducted in a reaction-inert solvent such as, for example, an ether e.g. tetrahydrofuran and preferably in the presence of a strong base, e.g. NaH.

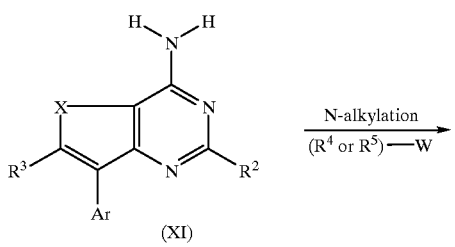

(XI)

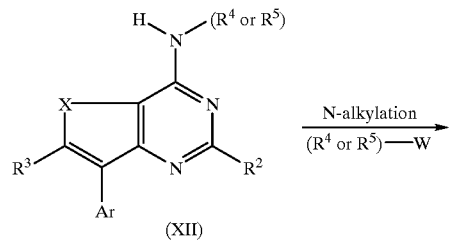

(XII)

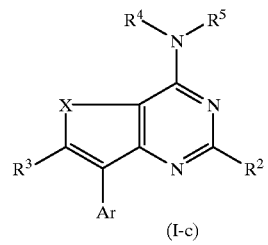

(I-c)

In certain instances, this reaction can give rise to side products wherein $R^2$ is alkylated by $(R^4$ or $R^5)$—W, in particular where $R^2$ is methyl and $R^4$ or $R^5$ is lower alkyl.

As outlined below, compounds of formula (I) may be converted into each other following art-known transformation procedures.

For instance, compounds of formula (I) wherein X is S can be converted into compounds of formula (I) wherein X is SO or $SO_2$ by an oxidation reaction, e.g. treatment with a peroxide such as 3-chloroperbenzoic acid in a reaction-inert solvent, e.g. dichloromethane. By controlling the amount of oxidant and other reaction parameters, either compounds of formula (I) wherein X is SO or X is $SO_2$ can be obtained, or a mixture of both, which subsequently can be separated by conventional methods, e.g. column chromatography. Also, the compounds of formula (I) wherein $R^3$ is $C_{1-6}$alkylthio can be converted into compounds of formula (I) wherein $R^3$ is $C_{1-6}$alkylsulfonyl or $C_{1-6}$alkylsulfoxy by an oxidation reaction similar as above described. By controlling the amount of oxidant and other reaction parameters, and by separating the end products, the various oxidated products can be separately obtained.

Further, the Ar group of compounds of formula (I) can be halogenated using a halogenating agent such as, e.g. chlorine or bromine, in a suitable solvent, e.g. acetic acid, and optionally the reaction may be performed at a temperature ranging between room temperature and the reflux temperature of the reaction mixture.

Stereoisomers may be prepared by separation of the end products of formula (I) following art-known procedures, e.g. by treatment with an optically active acid and separating the thus-formed diastereoisomeric salts by selective crystallization or column chromatography. Or, stereoisomers may be prepared by using stereoisomeric starting materials in any of the above reaction schemes or in the preparation of intermediates described hereinafter.

Intermediates of formula (II) wherein X is S, said intermediates being represented by compounds of formula (II-a), can be prepared as outlined herebelow. Intermediates of formula (VI) are prepared by treating intermediates of formula (IV) with an ester of formula (V) in a reaction-inert solvent such as an alcohol, e.g. ethanol, preferably in the presence of a strong base such as, e.g. sodium ethoxide or sodium hydride. The intermediates (VI) are reacted with methanesulphonyl chloride and subsequently with 2-(acetylthio)-acetonitrile, yielding aminothiophene derivatives of formula (VII). These are converted into intermediates (VIII) using conventional acylation methods such as, e.g. the use of an acid anhydride (R²CO)₂O. Intermediates of formula (VIII) are cyclized to intermediates (II'-b), in which the hydroxy group is converted into leaving group W, e.g. by treating intermediate (II'-b) with methanesulfonyloxy chloride or a halogenating reagent such as, e.g. POCl₃, thus yielding intermediates (II-a).

antagonizing activities associated with CRF. A compound of structure (I) may be assessed for activity as a CRF antagonist by one or more generally accepted assays for this purpose, including (but not limited to) the assays disclosed by DeSouza et al. (*J. Neuroscience* 7:88, 1987) and Battaglia et al. (*Synapse* I:572, 1987). As mentioned above, suitable CRF antagonists include compounds which demonstrate CRF receptor affinity. CRF receptor affinity may be determined

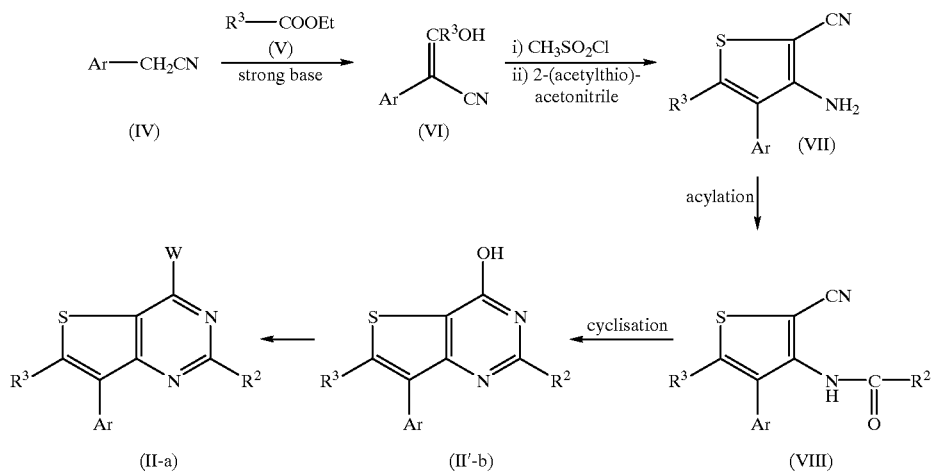

Intermediates of formula (XI) are prepared by treating intermediates of formula (II) with ammonia.

In an embodiment, this invention also provides for compounds of formula (II'-a), defined as compounds of formula (II-a) wherein W' represents hydroxy, halo, mesyloxy or tosyloxy; provided that 2-methyl-7-phenyl-thieno[3,2-d] pyrimidin-4(1H)-one is excluded.

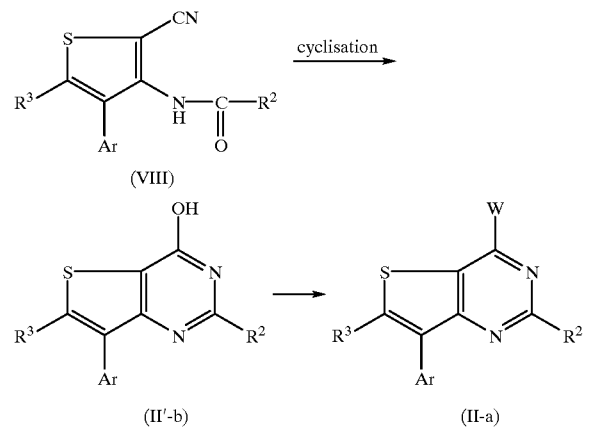

Said intermediates of formula (II'-a) may be prepared according to procedures used to prepare intermediates of formula (II-a), thereby thereby yielding compounds of formula (II'-b), defined as compounds of formula (II'-a) wherein W' is hydroxy; and optionally converting compounds of formula (II'-b) into compounds of formula (II'-a), defined as compounds of formula (II'-a) wherein W' is other than hydroxy.

The effectiveness of a compound as a CRF receptor antagonist may be determined by various assay methods. Suitable CRF antagonists of this invention are capable of inhibiting the specific binding of CRF to its receptor and by binding studies that measure the ability of a compound to inhibit the binding of a radiolabeled CRF (e.g. [$^{125}$I]tyrosine CFR) to receptor (e.g., receptors prepared from rat cerebral cortex membranes). The radioligand binding assay described by DeSouza et al. (supra, 1987) provides an assay for determining a compound's affinity for the CRF receptor. Such activity is typically calculated from the, IC$_{50}$ as the concentration of a compound necessary to displace 50% of the radiolabeled ligand from the receptor, and is reported as a "$K_i$" value calculated by the following equation:

$$K_i = \frac{IC_{50}}{1 + L/K_D}$$

where L=radioligand and $K_D$=affinity of radioligand for receptor (Cheng and Prusoff, *Biochem. Pharmacol.* 22:3099, 1973).

In addition to inhibiting CRF receptor binding, a compound's CRF receptor antagonist activity may be established by the ability of the compound to antagonize an activity associated with CRF. For example, CRF is known to stimulate various biochemical processes, including adenylate cyclase activity. Therefore, compounds may be evaluated as CRF antagonists by their ability to antagonize CRF-stimulated adenylate cyclase activity by, for example, measuring cAMP levels. The CRF-stimulated adenylate cyclase activity assay described by Battaglia et al. (supra, 1987) provides an assay for determining a compound's ability to antagonize CRF activity. Accordingly, CRF receptor antagonist activity may be determined by assay techniques which generally include an initial binding assay (such as disclosed by DeSouza (supra, 1987)) followed by a cAMP screening protocol (such as disclosed by Battaglia (supra, 1987)).

With reference to CRF receptor binding affinities, CRF receptor antagonists of this invention have a $K_i$ of less than 10 μM. In a preferred embodiment of this invention, a CRF receptor antagonist has a $K_i$ of less than 1 μM, and more preferably less than 0.25 μM (i.e., 250 nM).

The CRF receptor antagonists of the present invention demonstrate activity at the CRF receptor site, and may be used as therapeutic agents for the treatment of a wide range of disorders or illnesses including endocrine, psychiatric, and neurologic disorders or illnesses. More specifically, the CRF receptor antagonists of the present invention may be useful in treating physiological conditions or disorders arising from the hypersecretion of CRF. Because CRF is believed to be a pivotal neurotransmitter that activates and coordinates the endocrine, behavioral and automatic responses to stress, the CRF receptor antagonists of the present invention can be used to treat neuropsychiatric disorders. Neuropsychiatric disorders which may be treatable by the CRF receptor antagonists of this invention include affective disorders such as depression; anxiety-related disorders such as generalized anxiety disorder, panic disorder, obsessive-compulsive disorder, abnormal aggression, cardiovascular abnormalities such as unstable angina and reactive hypertension; and feeding disorders such as anorexia nervosa, bulimia, and irritable bowel syndrome. CRF antagonists may also be useful in treating stress-induced immune suppression associated with various diseases states, as well as stroke. Other uses of the CRF antagonists of this invention include treatment of inflammatory conditions (such as rheumatoid arthritis, uveitis, asthma, inflammatory bowel disease and G.I. motility), Cushing's disease, infantile spasms, epilepsy and other seizures in both infants and adults, and various substance abuse and withdrawal (including alcoholism).

In another embodiment of the invention, pharmaceutical compositions containing one or more CRF receptor antagonists are disclosed. For the purposes of administration, the compounds of the present invention may be formulated as pharmaceutical compositions. Pharmaceutical compositions of the present invention comprise a CRF receptor antagonist of the present invention (i.e., a compound of structure (I)) and a pharmaceutically acceptable carrier and/or diluent. The CRF receptor antagonist is present in the composition in an amount which is effective to treat a particular disorder, that is, in an amount sufficient to achieve CRF receptor antagonist activity, and preferably with acceptable toxicity to the patient. Preferably, the pharmaceutical compositions of the present invention may include a CRF receptor antagonist in an amount from 0.1 mg to 250 mg per dosage depending upon the route of administration, and more preferably from 1 mg to 60 mg. Appropriate concentrations and dosages can be readily determined by one skilled in the art.

Pharmaceutically acceptable carrier and/or diluents are familiar to those skilled in the art. For compositions formulated as liquid solutions, acceptable carriers and/or diluents include saline and sterile water, and may optionally include antioxidants, buffers, bacteriostats and other common additives. The compositions can also be formulated as pills, capsules, granules, or tablets which contain, in addition to a CRF receptor antagonist, diluents, dispersing and surface active agents, binders, and lubricants. One skilled in this art may further formulate the CRF receptor antagonist in an appropriate manner, and in accordance with accepted practices, such as those disclosed in *Remington's Pharmaceutical Sciences,* Gennaro, Ed., Mack Publishing Co., Easton, USA, 1990.

In another embodiment, the present invention provides a method for treating a variety of disorders or illnesses, including endocrine, psychiatric and neurologic disorders or illnesses. Such methods include administering of a compound of the present invention to a warm-blooded animal in an amount sufficient to treat the disorder or illness. Such methods include systemic administration of a CRF receptor antagonist of this invention, preferably in the form of a pharmaceutical composition. As used herein, systemic administration includes oral and parenteral methods of administration. For oral administration, suitable pharmaceutical compositions of CRF receptor antagonists include powders, granules, pills, tablets, and capsules as well as liquids, syrups, suspensions, and emulsions. These compositions may also include flavorants, preservatives, suspending, thickening and emulsifying agents, and other pharmaceutically acceptable additives. For parental administration, the compounds of the present invention can be prepared in aqueous injection solutions which may contain, in addition to the CRF receptor antagonist, buffers, antioxidants, bacteriostats, and other additives commonly employed in such solutions.

As mentioned above, administration of a compound of the present invention can be used to treat a wide variety of disorders or illnesses. In particular, the compounds of the present invention may be administered to a warm-blooded animal for the treatment of depression, anxiety disorder, panic disorder, obsessive-compulsive disorder, abnormal aggression, unstable angina, reactive hypertension, anorexia nervosa, bulimia, irritable bowel syndrome, stress-induced immune suppression, stroke, inflammation, Cushing's disease, infantile spasms, epilepsy, and substance abuse or withdrawal.

Hence, the use of a compound of formula (I) as a medicine is provided

The following examples are provided for purposes of illustration, not limition.

Experimental Part

Hereinafter "THF" means tetrahydrofuran, "DCM" means dichloromethane, "DMSO" means dimethylsulfoxide and "ACN" means acetonitrile.

A. Preparation of the Intermediates

EXAMPLE A.1 a) A solution of 2,4,6-trimethylphenylacetonitrile (75 g) and ethyl formate (67 g) in 225 ml absolute ethanol was treated with solid sodium ethoxide (36 g) in small portions over 10 minutes, with good stirring. The mixture was heated to 60° C. under nitrogen for 16 hours and allowed to cool to room temperature. The reaction mixture was poured into 1.2 liters of water, extracted with diethyl ether (3×200 ml). The aqueous phase was acidified with 6M HCl to pH=1 and extracted with ethyl acetate. The ethyl acetate extract was washed with brine, dried over $MgSO_4$ and concentrated, yielding 46 g (98%) of 3-hydroxy-2-(2,4,6-trimethylphenyl) acrylonitrile (intermediate 1).

b) A solution of intermediate 1 (1 g) in 10 ml pyridine was cooled to 0° C. under nitrogen and then treated with methanesulfonyl chloride (0.67 g) with good stirring. The solution was allowed to come to room temperature and stirred for 1 hour. The reaction mixture was poured into water and extracted with ethyl acetate. The organic phase was washed with 1M HCl, water and brine, dried ($MgSO_4$) and concentrated to give 3-methanesulfonyl-2-(2,4,6-trimethylphenyl) acrylonitrile (intermediate 2) as a brown solid (1.4 g).

c) To a suspension of NaOEt (3.7 g) in 40 ml of DMSO was added 2-(acetylthio)acetonitrile. After 30 minutes, a solution of intermediate 2 (13.2 g) in THF (80 ml) was added. $LiN(TMS)_2$ (1.0M in THF, 100 ml) was added via a syringe. The reaction was quenched with approximately 1 equivalent of acetic acid, after 1 hour at room temperature. After removing most of the THF by evaporation, the residue was dissolved in 500 ml of ethyl acetate and extracted twice with 500 ml water. The crude 2-cyano-3-amino-4-(2,4,6-trimethylphenyl)-thiophene (intermediate 3) (6.0 g) was carried on to the next step without further purification.

d) To a solution of intermediate 3 (6.0 g) in acetic acid (6 ml) was added acetic anhydride (5 g). The reaction mixture was stirred for 1 hour at 110° C. After cooling, the crude mixture was poured into a mixture of ethyl acetate (400 ml), water (600 ml) and saturated NaHCO$_3$ (200 ml). The organic layer was rinsed with water and concentrated. The residue was purified by column chromatography on SiO$_2$ (gradient; hexane:diethyl ether=2:1 to hexane:ethyl acetate=1:1) to give N-[2-cyano-4-(2,4,6-trimethylphenyl)-thiophen-3-yl]-acetamide (intermediate 4).

e) A suspension of intermediate 4 (2.8 g) in 85% of H$_3$PO$_4$ (2 ml) was stirred under nitrogen with an oil bath temperature of 130° C. for 30 minutes. After cooling, 20 ml of water was poured into this mixture. After mixing to induce precipitation, the resulting solid was filtered and dried in a vacuum oven to give 2.7 g of 3-methyl-6-hydroxy-8-(2,4,6,-trimethylphenyl)-thiopheno[3,2-d]pyrimidine (intermediate 5).

f) A suspension of intermediate 5 (2.6 g) in POCl$_3$ (8.0 g) was stirred for 2 hours at 100° C. After cooling, the mixture was poured into a mixture of saturated NaHCO$_3$ and DCM (100 ml). The organic phase was removed, concentrated in vacuo and the residue was purified by column chromatography on SiO$_2$ (gradient; ethyl acetate:hexane=1:4 to ethyl acetate:methanol=4:1) to give 0.3 g of 2-methyl-6-chloro-8-(2,4,6-trimethyl-phenyl)-thiopheno[3,2-d]pyrimidine (intermediate 6).

Table 1 lists the intermediates that were prepared according to example A.1.

TABLE 1

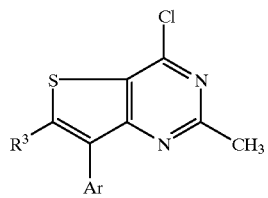

| Interm. No. | R$^3$ | Ar |
|---|---|---|
| 6 | CH$_3$ | 2,4,6-trimethylphenyl |
| 7 | CH$_3$ | 2,6-dimethyl-3-pyridinyl |
| 8 | CH$_3$ | 4-chlorophenyl |
| 9 | CH$_3$ | 6-(dimethylamino)-4-methyl-3-pyridinyl |
| 10 | CH$_3$ | 6-(diethylamino)-4-methyl-3-pyridinyl |
| 11 | CH$_3$ | 4,6-dimethyl-3-pyridinyl |
| 12 | H | 2,4,6-trimethyl-3-pyridinyl |
| 13 | H | 6-(dimethylamino)-2,4-dimethyl-3-pyridinyl |
| 14 | H | 2,4,6-trimethylphenyl |
| 15 | CH$_3$ | 4-methoxyphenyl |
| 16 | CH$_3$ | 2,4-dimethoxyphenyl |

B. Preparation of the Final Products

EXAMPLE B.1

A solution of intermediate 6 (20 mg) with N,N-dipropylamine in a 3 ml reaction vial was stirred at 120° C. After 1 hour the reaction mixture was cooled, 0.5 ml of acetonitrile was added and refluxed for another 30 minutes. The resulting suspension was allowed to cool to room temperature and diluted with additional acetonitrile. The residue was purified using SiO$_2$ column chromatography (diethyl ether/hexanes) to give 2-methyl-6-(N,N-dipropylamino)-8-(2,4,6-trimethylphenyl)-thiopheno[3,2-d]pyrimidine (compound 1).

EXAMPLE B.2

Treatment of intermediate 6 with sodium hydride and 2-propanol in THF and purification using SiO$_2$ column chromatography gave 2-methyl-6-(isopropoxy)-8-(2,4,6-trimethyl-phenyl)-thiopheno[3,2-d]pyrimidine (compound 6).

EXAMPLE B.3

A solution of compound 1 (5 mg) in 1 ml DCM was treated with meta-chloro-perbenzoic acid (20 mg). This solution was stirred for 24 hours, then poured into a mixture of ethyl acetate and water. The organic phase was washed with 5% aqueous NaHCO$_3$ solution and brine, dried (MgSO$_4$) and concentrated. The residue was purified by preparative TLC (diethyl ether/hexane: 1/9) to give 2-methyl-6-(N,N-dipropylamino)-8-(2,4,6-trimethylphenyl)-thiopheno[3,2-d]pyrimidine-S,S-dioxide (compound 7).

EXAMPLE B.4

Compound 2 (0.05 mmol) was stirred with excess bromine in 1 ml of acetic acid at room temperature for 30 minutes. The mixture was poured into a mixture of DCM and saturated aqueous NaHCO$_3$ and the organic layer was evaporated. The residue was purified by SiO$_2$ chromatography (diethyl ether/hexane), yielding 2-methyl-6-N-propyl-N-cyclopropylamino)-8-(3-bromo-2,4,6-trimethylphenyl)thiopheno[3,2-d]pyrimidine (compound 5).

Tables 2, 3 and 4 list the compounds that were prepared according to one of the above Examples and table 5 and 6 list the analytical data for these compounds.

TABLE 2

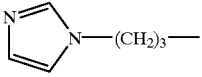

| Co. No. | Ex. No. | R³ | R⁴ | R⁵ |
|---|---|---|---|---|
| 1 | B.1 | H | n-propyl | n-propyl |
| 2 | B.1 | H | n-propyl | cyclopropylmethyl |
| 3 | B.1 | H | hydrogen | 3-pentyl |
| 4 | B.1 | H | n-propyl | 2-methoxyethyl |
| 9 | B.1 | H | hydrogen | $(CH_3)_2N(CH_2)_3$ |
| 10 | B.1 | H | $CH_3O(CH_2)_2$ | $CH_3O(CH_2)_2$ |
| 11 | B.1 | H | hydrogen | 4-methoxyphenylmethyl |
| 12 | B.1 | H | hydrogen | $CH_3O(CH_2)_2$ |
| 13 | B.1 | H | n-propyl | 2-hydroxyethyl |
| 14 | B.1 | H | hydrogen | 4-trifluoromethylphenylmethyl |
| 15 | B.1 | H | hydrogen | 3-hydroxypropyl |
| 16 | B.1 | H | hydrogen | 1-hydroxy-2-hexyl |
| 17 | B.1 | H | hydrogen | 1-hydroxy-2-pentyl |
| 18 | B.1 | H | hydrogen | 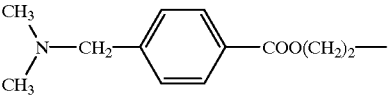 |
| 19 | B.1 | H | hydrogen | $CH_3CH_2-S-(CH_2)_2$ |
| 20 | B.1 | H | hydrogen | $CH_3-S-(CH_2)_2$ |
| 21 | B.1 | H | hydrogen | $(CH_3)_2N$ |
| 22 | B.1 | H | hydrogen | 2-ethoxyphenylmethyl |
| 23 | B.1 | H | n-propyl | $CH_3CH_2-CO-(CH_2)_2$ |
| 24 | B.1 | H | hydrogen | n-propyl |
| 25 | B.1 | H | hydrogen | butyl |
| 26 | B.1 | H | ethyl | 3-hydroxypentyl |
| 27 | B.1 | H | n-propyl | 3-hydroxypentyl |
| 28 | B.1 | H | n-butyl | 3-hydroxypentyl |
| 29 | B.1 | H | n-propyl | 3-hydroxybutyl |
| 30 | B.1 | H | n-butyl | 3-hydroxybutyl |
| 31 | B.1 | H | n-propyl | 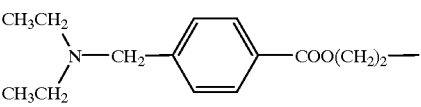 |
| 32 | B.1 | H | n-propyl | 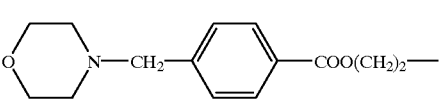 |
| 33 | B.1 | H | n-propyl | 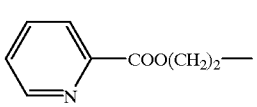 |
| 34 | B.1 | H | n-propyl | |
| 35 | B.1 | H | hydrogen | 4-morpholinyl |

TABLE 2-continued
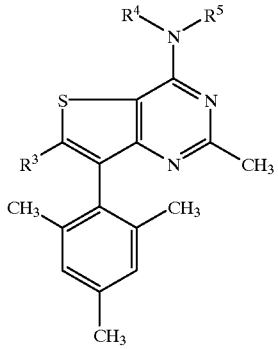
| Co. No. | Ex. No. | R³ | R⁴ and R⁵ taken together |
|---|---|---|---|
| 36 | B.1 | H | 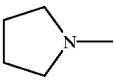 |
| 37 | B.1 | H | 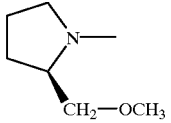 |
| 38 | B.1 | H | 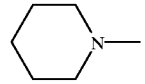 |
| 39 | B.1 | H | 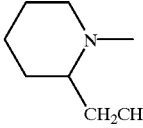 |
| 40 | B.1 | H | 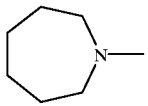 |

TABLE 3

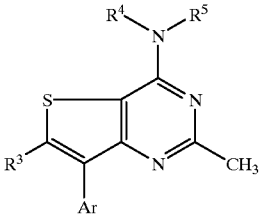

| Co. No. | Ex. No. | R³ | R⁴ | R⁵ | Ar |
|---|---|---|---|---|---|
| 5 | B.4 | H | n-propyl | cyclopropylmethyl | 3-bromo-2,4,6-trimethylphenyl |
| 8 | B.1 | CH₃ | n-propyl | n-propyl | 2,6-dimethyl-3-pyridinyl |
| 41 | B.1 | CH₃ | n-propyl | n-propyl | 4-chlorophenyl |
| 42 | B.1 | CH₃ | n-propyl | 2-hydroxyethyl | 4-chlorophenyl |
| 43 | B.1 | CH₃ | n-propyl | n-propyl | 6-(dimethylamino)-4-methyl-3-pyridinyl |
| 44 | B.1 | CH₃ | n-propyl | n-propyl | 6-(diethylamino)-4-methyl-3-pyridinyl |
| 45 | B.1 | CH₃ | n-propyl | n-propyl | 4-methoxyphenyl |
| 46 | B.1 | CH₃ | n-propyl | 2-methoxyethyl | 4-methoxyphenyl |
| 47 | B.1 | CH₃ | 2-methoxyethyl | 2-methoxyethyl | 4-methoxyphenyl |
| 48 | B.1 | CH₃ | n-propyl | n-propyl | 2,4-dimethoxyphenyl |
| 49 | B.1 | CH₃ | 2-methoxyethyl | 2-methoxyethyl | 2,4-dimethoxyphenyl |
| 50 | B.1 | CH₃ | n-propyl | n-propyl | 4,6-dimethyl-3-pyridinyl |
| 51 | B.1 | CH₃ | ethyl | n-butyl | 4,6-dimethyl-3-pyridinyl |
| 52 | B.1 | CH₃ | n-propyl | cyclopropylmethyl | 4,6-dimethyl-3-pyridinyl |
| 53 | B.1 | H | n-propyl | cyclopropylmethyl | 6-(dimethylamino)-2,4-dimethyl-3-pyridinyl |
| 54 | B.1 | H | n-propyl | n-propyl | 6-(dimethylamino)-2,4-dimethyl-3-pyridinyl |
| 55 | B.1 | H | n-propyl | 2-hydroxyethyl | 2,4,6-trimethylphenyl |
| 56 | B.1 | H | n-propyl | CH₃COO(CH₂)₂ | 2,4,6-trimethylphenyl |
| 57 | B.1 | H | n-propyl | 2-hydroxypropyl | 2,4,6-trimethylphenyl |
| 58 | B.1 | H | n-propyl | n-propyl | 2,4,6-trimethylphenyl |

| Co. No. | Ex. No. | R³ | R⁴ and R⁵ taken together | Ar |
|---|---|---|---|---|
| 59 | B.1 | H | 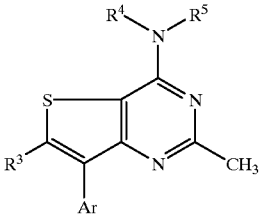 | 2,4,6-trimethylphenyl |
| 60 | B.1 | CH₃ | 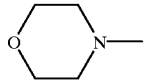 | 4-chlorophenyl |

TABLE 4

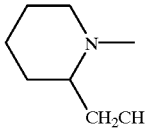

| Co. No. | Ex. No. | X | R¹ | Ar |
|---|---|---|---|---|
| 6 | B.2 | S | (CH₃)₂CH—O— | 2,4,6-trimethylphenyl |
| 7 | B.3 | SO₂ | (CH₃CH₂CH₂)₂N— | 2,4,6-trimethylphenyl |

TABLE 5

Analytical data

| Co. No. | ¹HNMR data (CDCl₃) |
|---|---|
| 1 | δ0.98(t, J=7.0Hz, 6H), 1.76(m, 4H), 1.99(s, 6H), 2.30(s, 3H), 2.45(s,3H), 3.69(t, J=7.5Hz, 6H), 6.93(s, 2H), 7.36(s, 1H) |
| 2 | δ0.37(m, 2H), 0.59(m, 2H), 1.02(t, J=7.5Hz, 3H), 1.25(m, 1H), 1.85(m, 2H), 2.01(s, 6H), 2.34(s, 3H), 2.48(s, 3H), 3.69(d, 2H), 3.80(m, 2H), 6.96(s, 2H), 7.40(s, 1H) |
| 3 | δ0.97(t, J=7.0Hz, 6H), 1.70(m, 4H), 2.01(s, 6H), 2.31(s, 3H), 2.50(s, 3H), 4.40(m, 1H), 6.94(s, 2H), 7.36(s, 1H) |
| 4 | δ1.03(t, J=7.0Hz, 6H), 1.79(m, 2H), 2.01(s, 6H), 2.34(s, 3H), 2.47(s, 3H), 3.41(s, 3H), 3.73(t, J=7.5Hz, 2H), 3.80(t, J=7.0H, 2H), 3.97(t, J=7.0Hz, 2H), 6.97(s, 2H), 7.41(s, 1H) |
| 5 | δ0.37(m, 2H), 0.59(m, 2H), 1.02(t, J=7.5Hz, 3H), 1.25(m, 1H), 1.85(m, 2H), 1.95(s, 3H), 2.10(s, 3H), 2.43(s, 3H), 2.48(s, 3H), |

TABLE 5-continued

Analytical data

| Co. No. | ¹HNMR data (CDCl₃) |
|---|---|
| | 3.69(d, 2H), 3.80(m, 2H), 7.04(s, 1H), 7.37(s, 1H) |
| 6 | δ1.45(d, J=6.5Hz, 6H), 1.99(s, 6H), 2.32(s, 3H), 2.60(s, 3H), 5.75(m, 1H), 6.95(s, 2H), 7.40(s, 1H) |
| 8 | δ0.98(t, J=7.0Hz, 6H), 1.76(m, 4H), 1.99(s, 6H), 2.30(s, 3H), 2.45(s, 3H), 3.69(t, J=7.5Hz, 6H), 7.08(d, H), 7.38(d, 1H) |
| 48 | δ0.97(t, 6H), 1.76(m, 4H), 2.37(s, 3H), 2.47(s, 3H), 3.68(t, 4H), 3.74(s, 3H), 3.86(s, 3H), 6.61(2H), 7.22(2H) |
| 49 | δ2.37(s, 3H), 2.47(s, 3H), 3.38(s, 6H), 3.70(t, 4H), 3.74(s, 3H), 3.86(s, 3H), 4.03(t, 4H), 6.61(2H), 7.22(2H) |
| 56 | δ1.05(t, 3H), 1.89(m, 2H), 2.00(s, 6H), 2.07(s, 3H), 2.35(s, 3H), 2.48(s, 3H), 3.81(t, 2H), 3.99(t, 2H), 4.48(t, 2H), 6.97(2H), 7.47(1H) |

TABLE 6

Analytical data

| Co. No. | Mass spectra data |
|---|---|
| 9 | 368 (M⁺) |
| 10 | 399 (M⁺) |
| 11 | 403 (M⁺) |
| 12 | 341 (M⁺) |
| 13 | 370 (MH⁺) |
| 14 | 441 (M⁺) |
| 15 | 342 (MH⁺) |
| 16 | 384 (MH⁺) |
| 17 | 370 (MH⁺) |
| 18 | 392 (MH⁺) |
| 19 | 371 (M⁺) |
| 20 | 357 (M⁺) |
| 21 | 327 (MH⁺) |
| 22 | 417 (M⁺) |
| 23 | 410 (MH⁺) |
| 24 | 326 (MH⁺) |
| 25 | 340 (MH⁺) |
| 26 | 398 (MH⁺) |
| 27 | 412 (MH⁺) |
| 28 | 426 (MH⁺) |
| 29 | 398 (MH⁺) |
| 30 | 412 (MH⁺) |
| 31 | 531 (MH⁺) |
| 32 | 559 (MH⁺) |
| 33 | 573 (MH⁺) |
| 34 | 475 (MH⁺) |
| 35 | 368 (MH⁺) |
| 36 | 337 (M⁺) |
| 37 | 382 (MH⁺) |
| 38 | 351 (M⁺) |
| 39 | 379 (M⁺) |
| 40 | 365 (M⁺) |
| 41 | 373 (M⁺) |
| 42 | 376 (MH⁺) |
| 43 | 397 (M⁺) |
| 44 | 425 (M⁺) |
| 45 | 369 (M⁺) |
| 46 | 385 (M⁺) |
| 47 | 410 (M⁺) |
| 48 | — |
| 49 | — |
| 50 | 368 (M⁺) |
| 51 | 368 (M⁺) |
| 52 | 380 (M⁺) |
| 53 | 409 (M⁺) |
| 54 | 397 (M⁺) |
| 55 | 372 (M⁺) |
| 56 | — |
| 57 | 372 (M⁺) |
| 58 | 368 (M⁺) |
| 59 | 353 (M⁺) |
| 60 | 385 (M⁺) |

C. Pharmacological Examples

EXAMPLE C.1

Representative Compounds Having CRF Receptor Binding Activity

Compounds were evaluated for binding activity to the CRF receptor by a standard radioligand binding assay as generally described by DeSouza et al. (*J. Neurosci.* 7:88–1000, 1987) by utilizing various radiolabeled CRF ligands, the assay may be used to evaluate the binding activity of the compounds of the present invention with any CRF receptor subtype. Briefly, the binding assay involves the displacement of a radiolabeled CRF ligand from the CRF receptor. More specifically, the binding assay was performed in 1.5 ml Eppendorf tubes using approximately $1 \times 10^6$ cells per tube stably transfected with human CRF receptors. Each tube received about 0.1 ml of assay buffer (e.g., Dulbecco's phosphate buffered saline, 10 mM magnesium chloride, 20 μM bacitracin) with or without unlabeled sauvagine, urotensin I or CRF (final concentration, 1 μM) to determine nonspecific binding, 0.1 ml of [$^{125}$I] tyrosine—ovine CRF (final concentration ~200 pM or approximately the $K_D$ as determined by Scatchard analysis) and 0.1 ml of a membrane suspension of cells containing the CRF receptor. The mixture was incubated for 2 hours at 22° C. followed by the separation of the bound and free radioligand by centrifugation. Following two washes of the pellets, the tubes were cut just above the pellet and monitored in a gamma counter for radioactivity at approximately 80% efficiency. All radioligand binding data were analyzed using a non-linear least-square curve-fitting program. Binding activity corresponds to the concentration (nM) of the compound necessary to displace 50% of the radiolabeled ligand from the receptor. All compounds as listed in Tables 2–4 have a $K_i \leq 250$ nM. Compounds 1, 2, 8, 10, 12–18, 20, 23, 34, 35, 37–41, 43, 48–56 were found to show the best score in this test.

EXAMPLE C.2

CRF Stimulated Adenylate Cyclase Activity

The compounds of the present invention may also be evaluated by various functional testing. For example, the compounds of the present invention may be screened for CRF-stimulated adenylate cyclase activity. An assay for the determination of CRF-stimulated adenylate cyclase activity may be performed as generally described by Battaglia et al. (*Synapse* 1:572, 1987), with modifications to adapt the assay to whole cell preparations.

More specifically, the standard assay mixture may contain the following in a final volume of 0.5 ml: 2 mM L-glutamine, 20 mM HEPES, and 1 mM IMBX in DMEM buffer. In stimulation studies, whole cells with the transfected CRF receptors are plated in 24-well plates and incubated for 1 hour at 37° C. with various concentrations of CRF-related and unrelated peptides in order to establish the pharmacological rank-order profile of the particular receptor subtype. Following the incubation, the medium is aspirated, the wells rinsed once gently with fresh medium, and the medium aspirated. To determine the amount of intracellular cAMP, 300 μl of a solution of 95% ethanol and 20 mM aqueous hydrochloric acid is added to each well and the resulting suspensions are incubated at −20° C. for 16 to 18 hours. The solution is removed into 1.5 ml Eppendorf tubes and the wells washed with an additional 200 μl of ethanol/aqueous hydrochloric acid and pooled with the first fraction.

The samples are lyophilized and then resuspended with 500 μl sodium acetate buffer. The measurement of cAMP in the samples is performed using a single antibody kit. For the functional assessment of the compounds, a single concentration of CRF or related peptides causing 80% stimulation of cAMP production is incubated along with various concentrations of competing compounds ($10^{-12}$ to $10^{-6}$M).

D. Composition Examples

The following formulations exemplify typical pharmaceutical compositions in dosage unit form suitable for systemic or topical administration to warm-blooded animals in accordance with the present invention. "Active ingredient" (A.I.) as used throughout these examples relates to a compound of formula (I), a N-oxide form, a pharmaceutically acceptable acid or base addition salt or a stereochemically isomeric form thereof.

EXAMPLE D. 1

Oral Solutions 9 g of methyl 4-hydroxybenzoate and 1 g of propyl 4-hydroxybenzoate are dissolved in 4 l of boiling purified water. In 3 l of this solution are dissolved first 10 g of 2,3-dihydroxybutanedioic acid and thereafter 20 g of the A.I. The latter solution is combined with the remaining part of the former solution and 12 l of 1,2,3-propanetriol and 3 l of sorbitol 70% solution are added thereto. 40 g of sodium saccharin are dissolved in 0.5 l of water and 2 ml of raspberry and 2 ml of gooseberry essence are added. The latter solution is combined with the former, water is added q.s. to a volume of 20 l providing an oral solution comprising 5 mg of the A.I. per teaspoonful (5 ml). The resulting solution is filled in suitable containers.

EXAMPLE D.2

Capsules 20 g of the A.I., 6 g sodium lauryl sulfate, 56 g starch, 56 g lactose, 0.8 g colloidal silicon dioxide, and 1.2 g magnesium stearate are vigorously stirred together. The resulting mixture is subsequently filled into 1000 suitable hardened gelatin capsules, each comprising 20 mg of the A.I.

Example D.3

Film-coated Tablets

Preparation of Tablet Core

A mixture of 100 g of the A.I., 570 g lactose and 200 g starch is mixed well and thereafter humidified with a solution of 5 g sodium dodecyl sulfate and 10 g polyvinylpyrrolidone in about 200 ml of water. The wet powder mixture is sieved, dried and sieved again. Then there are added 100 g microcrystalline cellulose and 15 g hydrogenated vegetable oil. The whole is mixed well and compressed into tablets, giving 10.000 tablets, each comprising 10 mg of the active ingredient.

Coating

To a solution of 10 g methyl cellulose in 75 ml of denaturated ethanol there is added a solution of 5 g of ethyl cellulose in 150 ml of dichloromethane. Then there are added 75 ml of dichloromethane and 2.5 ml 1,2,3-propanetriol. 10 g of polyethylene glycol is molten and dissolved in 75 ml of dichloromethane. The latter solution is added to the former and then there are added 2.5 g of magnesium octadecanoate, 5 g of polyvinylpyrrolidone and 30 ml of concentrated colour suspension and the whole is homogenated. The tablet cores are coated with the thus obtained mixture in a coating apparatus.

EXAMPLE D.4

Injectable Solution 1.8 g methyl 4-hydroxybenzoate and 0.2 g propyl 4-hydroxybenzoate were dissolved in about 0.5 l of boiling water for injection. After cooling to about 50° C. there were added while stirring 4 g lactic acid, 0.05 g propylene glycol and 4 g of the A.I. The solution was cooled to room temperature and supplemented with water for injection q.s. ad 1 l volume, giving a solution of 4 mg/ml of A.I. The solution was sterilized by filtration and filled in sterile containers.

EXAMPLE D.5

Suppositories

3 Grams A.I. was dissolved in a solution of 3 grams 2,3-dihydroxybutanedioic acid in 25 ml polyethylene glycol 400. 12 Grams surfactant and 300 grams triglycerides were molten together. The latter mixture was mixed well with the former solution. The thus obtained mixture was poured into moulds at a temperature of 37 to 38° C. to form 100 suppositories each containing 30 mg/ml of the A.I.

What is claimed is:

1. A compound of formula

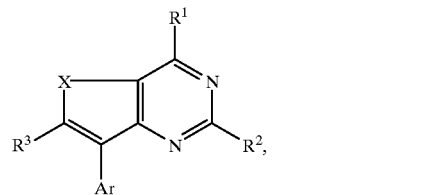

(I)

including the stereoisomers and the pharmaceutically acceptable acid addition salt forms thereof, wherein X is S, SO or $SO_2$;

$R^1$ is $NR^4R^5$ or $OR^5$;

$R^2$ is $C_{1-6}$alkyl, $C_{1-6}$alkyloxy or $C_{1-6}$alkylthio;

$R^3$ is hydrogen, $C_{1-6}$alkyl, $C_{1-6}$alkylsulfonyl, $C_{1-6}$alkylsulfoxy or $C_{1-6}$alkylthio;

$R^4$ is hydrogen, $C_{1-6}$alkyl, mono- or di($C_{3-6}$cycloalkyl)methyl, $C_{3-6}$cycloalkyl, $C_{3-6}$alkenyl, hydroxy$C_{1-6}$alkyl, $C_{1-6}$alkylcarbonyloxy$C_{1-6}$alkyl or $C_{1-6}$alkyloxy $C_{1-6}$alkyl;

$R^5$ is $C_{1-8}$alkyl, mono- or di($C_{3-6}$cycloalkyl)methyl, $Ar^1CH_2$, $C_{3-6}$alkenyl, $C_{1-6}$alkyloxy$C_{1-6}$alkyl, hydroxy$C_{1-6}$alkyl, thienylmethyl, furanylmethyl, $C_{1-6}$alkylthio$C_{1-6}$alkyl, morpholinyl, mono- or di ($C_{1-6}$alkyl)amino$C_{1-6}$alkyl, di($C_{1-6}$alkyl)amino, $C_{1-6}$alkylcarbonyl$C_{1-6}$alkyl, $C_{1-6}$alkyl substituted with imidazolyl; or a radical of formula —Alk—O—CO—$Ar^1$;

or $R^4$ and $R^5$ taken together with the nitrogen atom to which they are attached may form a pyrrolidinyl, piperidinyl, homopiperidinyl or morpholinyl group, optionally substituted with $C_{1-6}$alkyl or $C_{1-6}$alkyloxy$C_{1-6}$alkyl;

Ar is phenyl; phenyl substituted with 1, 2 or 3 substituents independently selected from halo, $C_{1-6}$alkyl, trifluoromethyl, hydroxy, cyano, $C_{1-6}$alkyloxy, benzyloxy, $C_{1-6}$alkylthio, nitro, amino and mono- or di($C_{1-6}$alkyl)amino; pyridinyl; pyridinyl substituted with 1, 2 or 3 substituents independently selected from halo, $C_{1-6}$alkyl, trifluoromethyl, hydroxy, cyano, $C_{1-6}$alkyloxy, benzyloxy, $C_{1-6}$alkylthio, nitro, amino, mono- or di($C_{1-6}$alkyl)amino and piperidinyl; and wherein said substituted phenyl may optionally be further substituted with one or more halogens;

$Ar^1$ is phenyl; phenyl substituted with 1, 2 or 3 substituents each independently selected from halo, $C_{1-6}$alkyl, $C_{1-6}$alkyloxy, di($C_{1-6}$alkyl)amino$C_{1-6}$alkyl trifluoromethyl, and $C_{1-6}$alkyl substituted with morpholinyl; or pyridinyl; and Alk is $C_{1-6}$alkanediyl.

2. A compound according to claim 1 wherein $R^1$ is $OR^5$ and $R^5$ is $C_{1-6}$alkyl; or $R^1$ is $NR^4R^5$ and $R^4$ is hydrogen, $C_{1-6}$alkyl or $C_{1-6}$alkyloxy$C_{1-6}$alkyl, and $R^5$ is $C_{1-6}$alkyl, hydroxy$C_{1-6}$alkyl, $C_{3-6}$alkenyl or $C_{3-6}$cycloalkylmethyl; or $R^1$ is $NR^4R^5$ and $R^4$ and $R^5$ are taken together with the nitrogen atom to which they are attached to form a pyrrolidinyl, piperidinyl, homopiperidinyl or morpholinyl group, optionally substituted with $C_{1-6}$alkyl or $C_{1-6}$alkyloxy$C_{1-6}$alkyl; $R^2$ is $C_{1-6}$alkyl; $R^3$ is hydrogen or $C_{1-6}$alkyl; and Ar is a phenyl substituted with 1, 2 or 3 substituents each independently selected from $C_{1-6}$alkyl, $C_{1-6}$alkyloxy or halo, or Ar is a pyridinyl substituted with 1, 2 or 3 substituents each independently selected from $C_{1-6}$alkyl or di($C_{1-6}$alkyl)amino.

3. A compound according to claim 2 wherein $R^1$ is $NR^4R^5$ wherein $R^4$ is $C_{2-4}$alkyl or methoxy$C_{1-2}$alkyl; $R^5$ is $C_{2-4}$alkyl, cyclopropylmethyl or hydroxy-$C_{2-4}$alkyl; $R^2$ is $C_{1-2}$alkyl; $R^3$ is hydrogen or $C_{1-2}$alkyl.

4. A compound according to claim 2 wherein $R^1$ is $NR^4R^5$ wherein $R^4$ is $C_{2-4}$alkyl; $R^5$ is $C_{3-4}$alkyl or cyclopropylmethyl; $R^2$ is methyl; $R^3$ is hydrogen or methyl; and Ar is 3-pyridinyl substituted on the 4- and/or 6-position with methyl or dimethylamino.

5. A compound according to claim 1 wherein the compound is
2-methyl-6-(N-propyl-N-cyclopropylamino)-8-(2,4,6-trimethylphenyl)-thiopheno[3,2-d]pyrimidine, and
2-methyl-6-(N,N-dipropylamino)-8-(2,4,6-trimethylphenyl)-thiopheno[3,2-d]pyrimidine; the stereochemically isomeric forms, or the pharmaceutically acceptable acid addition salts thereof.

6. A composition comprising a pharmaceutically acceptable carrier, and as active ingredient a therapeutically effective amount of a compound as claimed in any one of claims 1 to 5.

7. A process for preparing a composition as claimed in claim 6 characterized in that a therapeutically effective amount of said compound is intimately mixed with a pharmaceutically acceptable carrier.

8. A method of treating endocrine, psychiatric and neurologic disorders or illnesses comprising administering to a warm-blooded animal in need of treatment a therapeutically effective amount of a compound according to any one of claims 1–5.

9. A compound of formula (II'-a) wherein the radicals $R^2$, $R^3$ and Ar are as defined in any of claims 1 to 4 and radical W' is hydroxy, halo, mesyloxy or tosyloxy; a stereoisomeric form or an acid addition salt form thereof; with the proviso that 2-methyl-7-phenyl-thieno[3,2-d]pyrimidin-4(1H)-one is not included

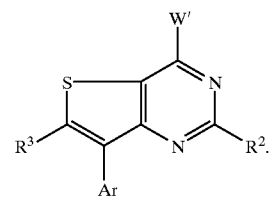

(II'-a)

10. A method for inhibiting a CRF receptor in a warm blooded animal comprising administering thereto a compound according to claim 1 in an amount therapeutically effective to antagonize said CRF receptor.

11. A method for treating a physiological condition or disorder in a warm blooded animal arising from the hypersecretion of corticotropin-releasing factor comprising administering to said animal a therapeutically effective amount of a compound according to claim 1.

12. The compound according to claim 1 wherein $R^5$ is $C_{1-8}$alkyl, $C_{3-6}$alkenyl, $C_{1-6}$alkyloxy$C_{1-6}$alkyl, hydroxy $C_{1-6}$alkyl, $C_{1-6}$alkylthio$C_{1-6}$alkyl, mono- or di-($C_{1-6}$alkyl) amino$C_{1-6}$alkyl, di($C_{1-6}$alkyl)amino, $C_{1-6}$alkylcarbonyl $C_{1-6}$alkyl; or a radical of the formula Alk—O—Co—$Ar^1$.

13. The compound according to claim 12 wherein $R_4$ is hydrogen, $C_{1-6}$alkyl, $C_{3-6}$alkenyl, hydroxy $C_{1-6}$alkyl, $C_{1-6}$alkylcarbonyloxy$C_{1-6}$alkyl or $C_{1-6}$alkyloxy$C_{1-6}$alkyl.

14. The compound according to claim 1 wherein X is SO or $SO_2$.

15. The compound according to claim 1 wherein $R_4$ and $R_5$ taken together with the nitrogen atom to which they are attached form a pyrrolidinyl, piperidinyl, homopiperidinyl or morpholinyl group, optionally substituted with $C_{1-6}$alkyl or $C_{1-6}$alkyloxy$C_{1-6}$alkyl.

16. The compound according to claim 1 wherein Ar is pyridinyl, substituted pyridinyl or piperidinyl.

17. The compound according to claim 16 wherein Ar is pyridinyl.

18. The compound according to claim 17 wherein Ar is 3-pyridinyl.

19. The compound according to claim 18 wherein Ar is 3-pyridinyl substituted in the 4 or 6 position with either methyl or dimethylamino.

20. The compound according to claim 18 wherein Ar is 3-pyridinyl which is disubstituted in the 4 and 6 positions with a methyl or dimethylamino and the substituents at the 4 and 6-position are either the same or different.

* * * * *